United States Patent [19]

Aas et al.

[11] Patent Number: 4,576,595

[45] Date of Patent: Mar. 18, 1986

[54] METHOD AND A CLOSURE CAP FOR SEALING A CAPILLARY TUBE

[75] Inventors: Flemming Aas, Soborg; Borge Jeppesen, Glostrup, both of Denmark

[73] Assignee: Radiometer A/S, Copenhagen, Denmark

[21] Appl. No.: 685,962

[22] Filed: Dec. 24, 1984

Related U.S. Application Data

[63] Continuation of Ser. No. 316,141, Oct. 29, 1981, abandoned.

[30] Foreign Application Priority Data

Oct. 31, 1980 [DK] Denmark ............................ 4618/80

[51] Int. Cl.[4] .......................... A61B 10/00; A61J 1/00

[52] U.S. Cl. .................................... 604/256; 128/763; 215/307; 215/355; 220/DIG. 19

[58] Field of Search ............................... 215/307, 355; 220/DIG. 19; 604/256; 128/763, 764

[56] References Cited

U.S. PATENT DOCUMENTS

| | | | |
|---|---|---|---|
| 1,700,227 | 1/1929 | Jeffery | 215/307 |
| 2,208,899 | 7/1940 | Freeman | 215/307 |
| 2,655,280 | 10/1953 | Cuttell et al. | 215/307 |
| 2,877,918 | 3/1959 | Gardner | 215/307 X |
| 3,118,578 | 1/1964 | Collins | 215/307 X |
| 3,307,552 | 3/1967 | Strawn | 604/256 |
| 3,888,382 | 6/1975 | Blumhardt | 215/307 X |
| 4,008,820 | 2/1977 | Ruetz | 215/355 X |
| 4,202,334 | 5/1980 | Elson | 215/355 X |

*Primary Examiner*—Horace M. Culver

*Attorney, Agent, or Firm*—Stiefel, Gross, Kurland & Pavane

[57] ABSTRACT

A capillary tube containing a sample is anaerobicly sealed by means of closure caps each comprising an end wall and a skirt portion. Each open end of the capillary tube is sealed by inserting the open tube end into the cap skirt portion, and in order to avoid that a volume of air is forced into the capillary tube, the space defined between the open tube end and the cap end wall is vented to the atmosphere through one or more venting passages defined in the walls of the closure cap or between the inner surface of the cap skirt portion and the adjacent outer peripheral surface of the capillary tube. The open tube end is brought into sealing engagement with sealing means on the cap end wall, and frictional engagement established between the inner surface of the cap skirt portion and adjacent outer peripheral surface parts of the capillary tube secures that said sealing engagement is maintained.

15 Claims, 19 Drawing Figures

METHOD AND A CLOSURE CAP FOR SEALING A CAPILLARY TUBE

This is a continuation of application Ser. No. 316,141, filed Oct. 29, 1981, and now abandoned.

BACKGROUND OF THE INVENTION

1. Field of the Invention

The present invention relates to a method of anaerobicly sealing an open end of a capillary tube, which is filled with a liquid sample, such as a blood sample. The invention also relates to a closure cap for sealing an open end of such capillary tube.

2. Description of the Prior Art

Anaerobic sampling of blood by using a capillary tube is well known in the art and is i.a. described by Ole Siggaard-Andersen on page 150 of a publication entitled "The Acid-Base Status of the Blood", fourth edition, issued by Munksgaard, Copenhagen 1974.

When such a capillary tube sample is used for determining the socalled blood gas parameters, namely pH, the partial pressure of oxygen ($pO_2$) and the partial pressure of carbon dioxide ($pCO_2$), it is extremely important that the blood sample is treated anaerobicly in the period of time from the sample is taken till it is analyzed. Therefore, it is necessary to seal the ends of the capillary tube by means of suitable means immediately after sampling.

The capillary tube may, for example, be closed as described in connection with FIG. 26 on page 150 of the above publication. According to the method disclosed in the above publication the sampling is carried out by positioning a heparinized capillary tube in a horizontal position adjacent to a puncture, so that blood may flow from that puncture into the tube by capillary effect without coming into contact with the atmosphere.

When the tube has been filled completely, one end thereof is sealed by means of a plastic sealing material kept in a cup or a box. This sealing is carried out by pressing the respective open end of the capillary tube approximately 4 mm into the sealing material. The sealing material will then be pressed into the open end of the tube, and a corresponding volume of blood will be expelled from the opposite end of the capillary tube.

A short length of a steel wire is now positioned within the tube, and the other open end of the tube is sealed by pressing the said end approximately 2 mm into the sealing material. This causes the sealing material in the first open end of the capillary tube to be displaced a corresponding length outwardly provided that the tube is completely filled with blood without gas bubbles. Thus, it is important that the second end of the capillary tube is sealed by pressing this end into the sealing material to a depth which is smaller than that used in sealing the first end of the capillary tube.

The sealing material which is frequently used for that purpose is a putty-like material marketed by Radiometer A/S under the designation Sealing Wax D 553 943-800. This material is packed in a small box and intended for several uses. The sealing material has such a surface area that is may be used for sealing about 50 capillary tubes. When the known method described above is used it it not possible to avoid that residues of blood are left in the sealing material. However, in connection with blood analysis it should always be attempted to avoid such residues, or they must be removed as soon as possible because the existence of such blood residues mean a potential risk of infection. Therefore, it is desirable to provide an alternative method of sealing capillary tubes.

Such an alternative method involving the use of closure caps has already been proposed. However, as explained in the following this alternative method is also disadvantageous.

Commercially available closure caps, which are described more in detail below in connection with FIG. 3 of the drawings, are made from a flexible material, and each cap comprises a skirt portion having an inner diameter corresponding to the outer diameter of the capillary tube, apart from a possible enlarged part at the open end of the skirt portion for facilitating mounting of the cap on the capillary tube end. By using these known closure caps, expulsion of blood from the capillary tube during the sealing procedure may be substantially avoided. This eliminates the risk of contamination and also the risk that a seal established at the first end of a capillary tube is broken by establishing a seal at the opposite tube end.

However, it is rather difficult to seal the open end of a capillary tube anaerobicly by means of a closure cap of the known type, because the closure cap must be held by one hand and compressed between a pair of fingers so as to expell air from the inner space of the cap skirt portion before mounting. The capillary tube may then be gripped by the other hand, and one end of the tube may be pushed into the skirt portion of the closure cap while the compressive force exerted on the skirt portion by the fingers is slowly released so that the end of the capillary tube may be brought into engagement with the inner surface of the cap end wall substantially without inclusion of air. However, correct mounting of the known closure caps requires a certain skill and experience, because it is difficult to ascertain whether the tube end has been brought into proper engagement with the cap end wall, or whether a small air volume has been entrapped in a space defined within the skirt portion between the tube end and the cap end wall in a compressed condition. In the latter case no anaerob sealing of the capillary tube is obtained.

German Offenlegungsschrift No. 2,848,535 discloses a device for sampling of blood by means of a capillary tube having one end thereof closed by a stopper having venting passages therein communicating the inner space of the capillary tube with the ambient atmosphere. Thus, the inner space of the tube is vented so that air may escape from the capillary tube when it is filled with blood. Thus, the stopper does not seal the capillary tube anaerobicly, but causes that samples having a rather accurate predetermined volume may be taken out by means of this known sampling device.

Further prior art is disclosed in German Offenlegungsschrift No. 2,906,209, published Swedish patent specification No. 358,552, and German Auslegeschrift No. 2,455,631.

SUMMARY OF THE INVENTION

The present invention provides a method and a closure cap facilitating anaerobic sealing of a capillary tube containing a liquid sample, such as blood.

Thus, the present invention provides a method of anaerobicly sealing an open end of a capillary tube, which is filled with a liquid sample, by means of a closure cap comprising an end wall and a skirt portion extending axially therefrom, said method comprising inserting said open tube end into said cap skirt portion so as to define a space between said tube end and said cap end wall, venting said space to the atmosphere while further inserting said tube end into said cap skirt portion so as to bring said open tube end into engagement with said cap end wall for sealing said open end, and establishing frictional engagement between inner surface parts of said cap skirt portion and adjacent outer surface parts of said capillary tube so as to retain said cap end wall in sealing engagement with said open tube end.

According to the present invention the inner space of the cap skirt portion is vented to the atmosphere while the open tube end is inserted into the skirt portion. Therefore, it is not necessary to expell air from the inner of the skirt portion by compressing the same, but the tube end to be sealed may right away be inserted into the skirt portion till the tube end comes into contact and sealing engagement with the inner surface of the cap end wall. Therefore, the method according to the invention is much more simple than the known method described above.

Sealing of the open tube end may be obtained by establishing a simple pressure contact between the annular end surface of the capillary tube and the inner surface of the cap end wall which may, for example, be made from a resilient material. However, in order to secure a sealing engagement also in case the said annular end surface of the capillary tube is not completely plane, but shows some irregularities, the open tube end may be brought into engagement with sealing means arranged on the inner surface of the cap end wall. Such sealing means may, for example, be in the form of a relatively thin layer of a plastic sealing material of the type mentioned above. However, in the preferred embodiment the said sealing means comprises a tapered, for example conical or frusto-conical, sealing member or stopper member extending axially from the inner surface of the cap end wall and being adapted to be received in the open tube end. In order to avoid expulsion of blood from the capillary tube, the said stopper member is rather short.

The passage or passages for venting the inner space of the skirt portion may extend transversely through the wall of the skirt portion adjacent to the cap end wall, or have any other suitable extension through the walls of the closure cap. In the preferred embodiment, however, the inner space of the skirt portion of the cap is vented through one or more passages defined between the inner surface of the cap skirt portion and the outer peripheral surface of the capillary tube. Thus, the venting passage or passages may be channels or grooves extending along the inner surface of the skirt portion. Such channels or grooves preferably extend axially and rectilinearly. However, they may have any other desired extension, such as a curved, helical, or tortuous extension.

Alternatively, the inner surface of the skirt portion may have a minimum diameter exceeding the outer diameter of the capillary tube so as to define an annular venting passage between the outer peripheral surface of the tube and the inner surface of said skirt portion. When the open tube has been brought into sealing engagement with the cap end wall, the desired frictional engagement between the inner surface of the cap skirt portion and the outer peripheral surface of the capillary tube may be obtained by inserting the tube end and the closure cap applied thereto through a restricted passage defined in a compression member so as to compress the cap skirt portion radially into contact with the outer surface of the capillary tube. When the closure cap is passed through such restricted passage, air will be expelled from the annular space defined between the outer surface of the capillary tube and the inner surface of the cap skirt portion. The last mentiond embodiment of the method according to the invention requires the use of a special compression member, which may be connected to or form part of the closure cap.

The present invention also provides a closure cap for anaerobicly sealing an open end of a capillary tube filled with a liquid sample, said cap comprising an end wall and an annular skirt portion extending axially therefrom, the inner surface of said end wall comprising means for sealingly engaging with said open tube end, and the inner surface of said skirt portion being adapted to frictionally engage with the outer peripheral surface of said capillary tube for maintaining said sealing means in engagement with said open tube end, at least one venting passage extending from the ambient atmosphere to a position adjacent to said inner surface of the cap end wall and being defined by the walls of said cap.

Said skirt portion is preferably made from an elastic material, and at least parts of the inner surface of the skirt portion may have an inner diameter corresponding to or being slightly smaller than the outer diameter of the capillary tube so as to obtain the desired frictional engagement between the skirt portion and the outer peripheral surface of the capillary tube. Thus, the cross section of the inner surface of the annular skirt portion may be non-circular at least adjacent to the cap end wall so as to define the venting passage or passages between the inner surface of the skirt portion and the outer peripheral surface of the capillary tube, and so as to simultaneously obtain the desired frictional engagement between the skirt portion and the capillary tube. In the preferred embodiment the cross section of the inner surface of the annular skirt portion engages the peripheral outer surface of the capillary tube at 3–6 peripherally spaced positions so as to define 3–6 venting passages between the inner surface of the skirt portion and the peripheral outer surface of the capillary tube. The said cross section of the inner surface of the skirt portion may, for example, be polygonal, for example triangular.

Alternatively, the inner surface of the skirt portion may have a cross section exceeding that of the outer surface of the capillary tube so as to define an annular space between the said surfaces in the mounted position of the cap, and the closure cap may then further comprise a skirt compression member having a passage defined therein with a cross section sized so as to compress the skirt portion radially inwardly into frictional engagement with the outer peripheral surface of the capillary tube when the tube end having the closure cap mounted thereon is inserted into said passage. The connecting means preferably comprises one or more flexible connecting members. Thus, the compression member may be connected to the skirt portion or to the cap end wall by means of one or more flexible bands or strips. The compression member and the skirt portion are then preferably interconnected so that the passage of the compression member and the skirt portion extend substantially coaxially on opposite sides of the cap end wall. In that case the connecting means may comprise a number of annularly arranged, peripherally spaced, flexible bands or strips, or a flexible tubular connecting member with or without openings or cutouts and extending coaxially with the skirt portion and the said passage. When an open end of a capillary tube has been inserted axially into the skirt portion of a closure cap, the tube end may be further moved axially in relation to the compression member, so that the tube end and the surrounding skirt portion are moved into the passage of the compression member, whereby the skirt portion is compressed axially into contact with the peripheral outer surface of the tube end.

BRIEF DESCRIPTION OF THE DRAWING

The invention will now be further described with reference to the drawings, wherein.

DESCRIPTION OF THE PREFERRED EMBODIMENTS

Figure 1A:
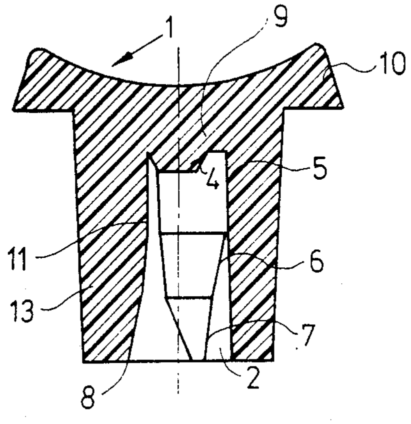
FIG. 1*a* is a sectional view of a first embodiment of the closure cap according to the invention along the line Ia—Ia in FIG. 1*b*.
Figure 1B:
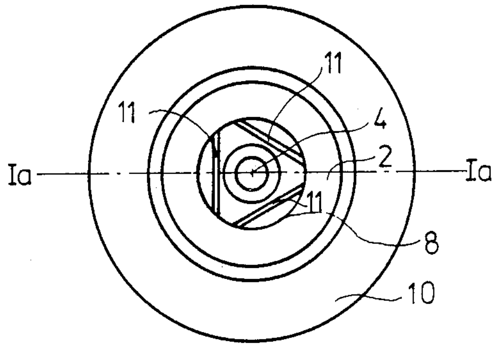
FIG. 1*b* is a bottom view of the closure cap shown in FIG. 1*a*, FIGS. 2*a*, 2*b* and 2*c* illustrate various stages of the process of mounting a closure cap as that shown in FIG. 1 on an open end of a capillary tube.

FIGS. 1*a* and 1*b* show a preferred embodiment of a closure cap 1 according to the invention. The closure cap comprises an annular skirt portion 13 which is closed at one end by an end wall 9 and open at the opposite end so as to define a blind passage or pocket 2 therein. The axial length of the pocket or passage 2 is divided into three sections 5, 6 and 7. The inner section 5 of the pocket 2 has a substantially triangular cross section, while the pocket 2 has a substantially circular outer opening 8, and the length sections 6 and 7 form transitional zones between the triangular and the circular cross sectional shapes. A closure member 4 in the form of a frusto-conical stopper member is formed on the inner surface of the end wall 9 which is also provided with a peripheral gripping flange 10.

As illustrated in FIG. 2 the closure cap 1 may be used for sealing an open end of a capillary tube 12 which may be filled with a liquid sample, such as a blood sample. The closure cap is preferably made of an elastic material, such as plastics, and the cross sectional shape of the section 5 of the passage 2 is dimensioned so that the outer peripheral surface of the capillary tube 12 is brought into frictional engagement with the inner walls of the section 5 along longitudinally extending zones 11 when an end portion of the tube 12 is inserted into the passage 2. Due to the triangular cross sectional shape of the section 5 longitudinally extending venting passages 3 will be defined between the outer peripheral surface of the tube 12 and the inner surface parts of the skirt portion 13 located between the longitudinal zones 11.

Figure 2A:
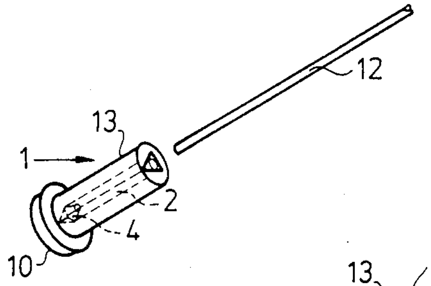
Figure 2B:
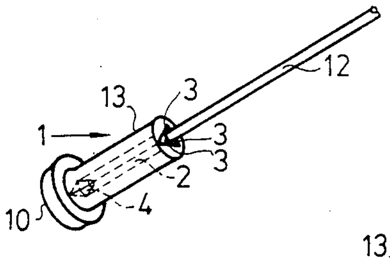
Figure 2C:
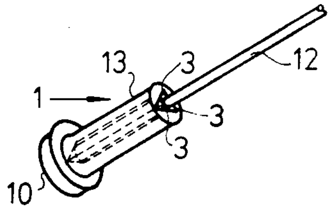

FIGS. 2*a*, 2*b* and 2*c* illustrate three different stages of the process of mounting a closure cap 1 as that shown in FIG. 1 on a capillary tube 12. For the sake of convenience the cap is shown more diagrammatically than in FIG. 1. FIG. 2*a* shows the closure cap 1 in an initial non-mounted condition. In FIG. 2*b* one of the open end portions of the capillary tube 12 has been inserted into the widened outer section 7 of the passage or pocket 2. This widened section serves as an insertion funnel. When the capillary tube 12 is pushed further into the pocket or passage 2 the outer peripheral surface of the tube eventually comes into frictional engagement with the inner wall of the inner passage section 5 along the longitudinal zones 11. Air in the space defined in the passage 2 between the end wall 9 and the inner end surface of the tube 12 may escape through the venting passages 3. Therefore, the open end of the tube 12 may be pushed so far into the pocket or passage 2 that the tapered stopper member 4 comes into engagement with the end opening of the tube 12 without any entrapping of air at the inner end of the pocket 2 or in the tube 12. The diameter of the stopper member 4 at the free end thereof is preferably somewhat smaller than the inner diameter of the tube 12, while the diameter of the stopper at the root portion thereof substantially corresponds to the inner diameter of the tube. Ind order to restrict displacement of the liquid sample within the tube 12 to a minimum when the stopper member 4 is inserted into the end opening of the tube, the length of the stopper member 4 is preferably relatively small, for example about 1/10 of the axial length of the passage or pocket 2. When the closure cap 1 has been mounted on the capillary tube 12 as shown in FIG. 2*c*, the respective end of the tube is anaerobicly sealed by the stopper member 4, and the frictional engagement between the skirt portion 13 and the outer surface of the capillary tube 12 along the zones 11 prevents that this seal becomes broken inadvertently.

The gripping flange 10 facilitates handling of the closure cap, especially in connection with mounting and demounting of the cap. The relationship between the wall thicknesses of the skirt portion 13, the end wall 9, and the gripping flange 10 is preferably chosen to that a possible deformation of the gripping flange 10 will not cause deformation of the walls defining the pocket or passage 2 with a consequent possible breaking of the anaerobic seal of the tube end.

Figure 3A:
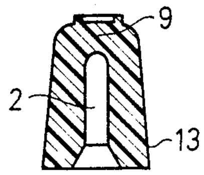
FIG. 3*a* is a sectional view of a closure cap of a known type along the line IIIa—IIIa in FIG. 3*b*.
Figure 3B:
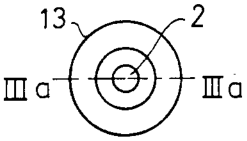
FIG. 3*b* is a bottom view of the closure cap shown in FIG. 3*a*.

FIGS. 3*a* and 3*b* illustrate a closure cap of a known type comprising an end wall 9 and a skirt portion 13 defining a pocket or passage 2 having a substantially cylindrical inner part having a wall fitting snugly around the outer peripheral surface of a capillary tube which is to be sealed. This known closure cap is made of a deformable material, and before the cap is mounted on a capillary tube it must be compressed between a pair of fingers in order to expell air from the cylindrical part of the pocket 2 in order to secure an anaerobic sealing. It is understood that proper mounting of such a known cap requires much more skill and care than mounting of a cap according to the invention. It is also more difficult to remove the known closure cap from a capillary tube than to remove a closure cap according to the invention.

Figure 4A:
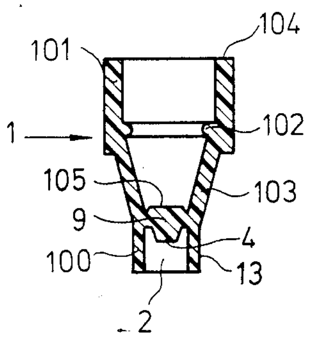
FIG. 4*a* is a sectional view of a second embodiment of the closure cap according to the invention along the line IVa—IVa in FIG. 4*b*.
Figure 4B:
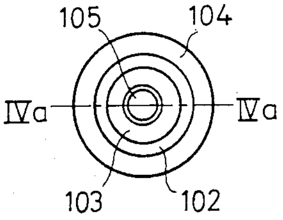
FIG. 4*b* is a bottom view of the closure cap shown in FIG. 4*a*.

FIGS. 4*a* and 4*b* show a further embodiment of the closure cap according to the invention. This embodiment comprises a cap portion 100 and a compression member or compression portion 101. The portions 100 and 101 are coaxially aligned and interconnected by means of a tubular, frusto-conical connecting member or connecting portion 103 which is made of a flexible material. The cap portion 100 defines a cylindrical pocket or blind passage 2 having an inner diameter slightly exceeding the outer diameter of the capillary tube to be closed by means of the closure cap, so that air may easily escape from the pocket 2 when an end of the capillary tube is inserted into the oversized pocket 2 and the end opening of the tube is brought into sealing engagement with the stopper member 4. The inner surface of the compression member 101 defines an annular ridge or bead 102 defining a compression passage. When the capillary tube has been brought into engagement with the stopper member 4, the tube and the cap portion 100 may be pressed axially towards and into the compression member 101 while the connecting member 103 is being deformed correspondingly. When the skirt portion of the cap member 100 is pushed through the passage defined by the annular ridge 102 the inner cylindrical wall of the skirt portion is pressed radially into frictional engagement with the outer surface of the capillary tube, and air is expelled from the skirt portion so as to secure the anaerobic sealing of the tube end. The axial distance between the ridge or bead 102 and the annular end surface 104 of the cap portion 100 is preferably shorter than the axial length of the cap member 100, so as to secure that the bead 102 is in engagement with the skirt portion of the cap member 100 when the cap member does not extend beyond the end surface 104. The last mounting step may then advantageously be made by placing the end surface 104 of the compression member 101 in contact with a plane supporting surface, such as the surface of a table, and thereafter pushing the capillary tube axially towards said supporting surface till the inner surface 105 of the cap member end wall is also brought into contact with the supporting surface and consequently is positioned in the same plane as the annular end surface 104.

FIGS. 5–9 show further embodiments of the closure cap according to the invention. Also these embodiments of the closure caps 1 have a pocket or blind passage 2, a tapered stopper member 4, and a flange 10 as described above.

Figure 5A:
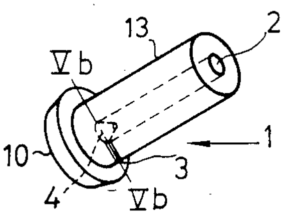
FIG. 5*a* is a perspective view of a third embodiment of the closure cap according to the invention.
Figure 5B:
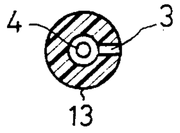
FIG. 5*b* is a sectional view of the closure cap shown in FIG. 5*a* along the line Vb—Vb.

In the embodiments shown in FIGS. 5*a* and 5*b* the passage 2 has a substantially cylindrical inner surface with a diameter corresponding to or being slightly smaller than the outer diameter of the capillary tube, so that a proper frictional engagement may be obtained. A venting passage 3 extending transversely through the skirt portion of the cap is venting the inner end of the passage 2 to the ambient atmosphere. When an end portion of a capillary tube is inserted into the passage or pocket 2, air may escape through the venting passage 3 so that no air is entrapped within the closure cap when the capillary tube has been brought into sealing engagement with the stopper member 4.

Figure 6A:
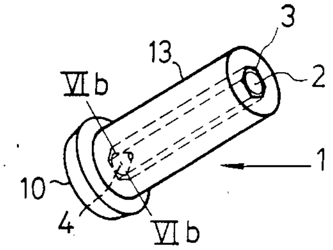
FIG. 6*a* is a perspective view of a fourth embodiment of the closure cap according to the invention.
Figure 6B:
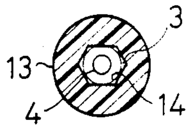
FIG. 6*b* is a sectional view along the line VIb—VIb in FIG. 6*a*.
Figure 7A:
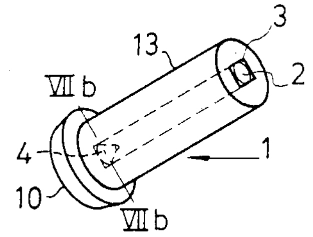
FIG. 7*a* is a perspective view of a fifth embodiment of the closure cap according to the invention.
Figure 7B:
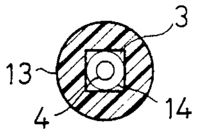
FIG. 7*b* is a sectional view along the line VIIb—VIIb in FIG. 7*a*.

FIGS. 6 and 7 show embodiments which in principle are similar to that shown in FIG. 1. However, while the inner section of the passage 2 has a substantially triangular cross sectional shape in FIG. 1, the cross section of the passages 2 in FIGS. 6 and 7 are shaped substantially as a regular hexagon and as a square, respectively. In FIGS. 6 and 7 the outer peripheral surface of a capillary tube which has been inserted into the cap 1, is indicated by a circle 14. From FIGS. 6*b* and 7*b* it appears that longitudinally extending venting passages 3 in a number of six and four, respectively, are defined in the closure caps shown in FIGS. 6 and 7, when capillary tubes are mounted therein.

Figure 8A:
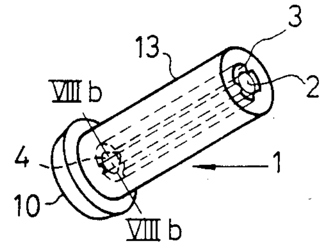
FIG. 8*a* is a perspective view of a sixth embodiment of the closure cap according to the invention.
Figure 8B:
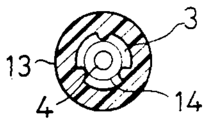
FIG. 8*b* is a sectional view along the line VIIIb—VIIIb in FIG. 8*a*.
Figure 9A:
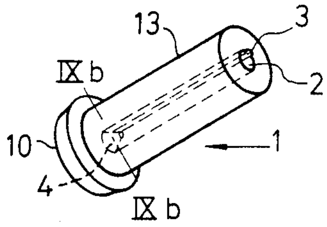
FIG. 9*a* is a perspective view of a seventh embodiment of the closure cap according to the invention.
Figure 9B:
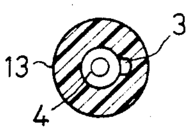
FIG. 9*b* is a sectional view along the line IXb—IXb in FIG. 9*a*.

FIGS. 8 and 9 illustrate additional embodiments, wherein the pocket or blind passage 2 also has a non-circular cross section so as to define one or more longitudinally extending venting passages between the capillary tube and the inner surface of the skirt portion. In FIG. 8*b* the venting passages are provided by three grooves or channels formed in the inner wall of the pocket 2, while only one groove or channel is provided in the embodiment of FIG. 9. It is understood that embodiments as those shown in FIGS. 5 and 9 normally give rise to a substantially higher friction between the cap skirt portion and the outer surface of the capillary tube than the other embodiments shown in the drawings. Such increased friction may be less desired as it renders the mounting and demounting of the closure cap excessively difficult.

It should be understood that the blind passages or pockets 2 in the embodiments shown in FIGS. 3–9 could be provided with widened open end portions like the embodiment shown in FIG. 1. The embodiments shown on the drawings could also be modified in various other manners. For example, the pocket or passage 2 may have any other cross sectional shapes than those illustrated provided that they allow air to escape from the pocket when the open end of the capillary tube is inserted therein and brought into sealing engagement with the cap end wall. The following are examples of such cross sectional shapes: non-regular polygons, shapes having the character of polygons, but having rounded or curved vertices and/or sides, generally circular shapes having one or more extensions in relation to the circular shape, and various kinds of lobed shapes in which a circle may be inscribed. The invention also comprises a closure cap, wherein the venting passage or passages is/are formed by one or more slits or slots extending from the free end of the skirt portion to the inner surface of the cap end wall.

The closure cap according to the invention is preferably made of a suitable polymer material by die casting. The criterion on suitability is primarily that the material must have such a modulus of elasticity that the closure cap may be used in connection with capillary tubes which may have diameters varying within certain limits and allow insertion and anaerobic sealing of such capillary tubes as well as retention of the cap in that sealing position on the tubes. A suitable material must also have a low frictional resistance and a low permeability to air and be unable to release undesired chemical substances therefrom. Such material suitable for closure caps according to the invention is a transparent polyvinyl chloride with a Shore-hardness of 50°–60°A.

COMPARATIVE TEST

In order to find out whether a closure cap as that shown in FIGS. 1*a* and 1*b* of the drawings and made of polyvinyl chloride with the above hardness may be used for sealing a capillary tube just as satisfactory as a conventional sealing by means of sealing wax of a well known type, a number of experiments were made with tonometered blood (tonometer gas 3.2% $O_2$, 5.7% $CO_2$ and the rest $N_2$). The parameters, oxygen saturation SAT and pH, were measured by measuring equipment marketed by Radiometer A/S, Copenhagen, under the designations OSM2 and BMS3MK2.

Two series of tests were made, and each included 10 capillary tubes. The measurements of the first series of tests were made immediately after sealing, and the measurements of the other series of tests were made after about 5 minutes of standing. In the second series of tests the contents of the capillary tubes were agitated by means of a pin included in each of the tubes immediately after filling and sealing of the tubes and also after the said 5 minutes of standing.

As mentioned above, each series of tests comprised measurement of 10 capillary tubes of which every second was sealed by means of the closure cap according to the invention, while the rest was sealed by means of sealing wax.

The following results were obtained:

TABLE I (without agitation)

| | Sealed by sealing wax | | Sealed by closure caps according to the invention | |
|---|---|---|---|---|
| | SAT % | pH | SAT % | pH |
| X | 46.0 | 7.356 | 46.1 | 7.357 |
| $S_o$ | 0.6 | 0.006 | 0.9 | 0.006 |

TABLE II (with agitation and standing)

| | Sealed by sealing wax | | Sealed by closure caps according to the invention | |
|---|---|---|---|---|
| | SAT % | pH | SAT % | pH |
| X | 43.3 | 7.319 | 43.4 | 7.317 |
| $S_o$ | 2.0 | 0.008 | 2.0 | 0.009 |

From the above tables I and II it appears that the average value X and the scatter $S_o$ of SAT and pH are almost identical for the two sealing methods. This shows that the effectivity of these two sealing methods is equal as far as protection against contamination is concerned.

We claim:

1. A closure cap for anaerobicly sealing an open end of a capillary tube having an inner and outer surface and being filled with a blood sample, said cap comprising an end wall having an inner surface and an annular skirt portion extending axially therefrom, the inner surface of said end wall comprising means for sealingly engaging with said open tube end the annular skirt having an inner surface of the skirt exceeding the cross section of the outer surface of the capillary tube thereby defining an annular space between the inner surface of the skirt portion and the outer surface of the capillary tube in the mounted position of the cap, said closure cap further comprising a skirt compression member having a passage defined therein for receiving said cap when mounted on said capillary tube, the cross section of said passage being sized so as to compress said skirt portion radially inwardly into frictional contact with the outer peripheral surface of the capillary tube when said cap skirt portion is inserted into said passage, whereby said end wall may be maintained in sealing engagement with said open tube end.

2. A closure cap according to claim 1, wherein said skirt compression member is connected to said skirt portion by flexible connecting means, said passage and said skirt portion extending substantially coaxially on opposite sides of said cap end wall.

3. A closure cap according to claim 2, wherein said passage is defined by an annular bead or ridge formed on an inner annular surface of said compression member.

4. A closure cap according to claim 3, wherein said annular ridge or bead is made from an elastic material.

5. In a blood sampling set of the type having an open ended capillary tube and a pair of closure caps for anaerobicly sealing both tube ends, wherein the improvement comprises: the closure caps, each cap having an end wall and an annular skirt portion extending axially therefrom, the inner surface of said end wall comprising means for sealingly engaging with a respective open tube end of said capillary tube, the cross section of the inner surface of the skirt exceeding the cross section of the outer surface of the capillary tube so as to define an annular space between the inner surface of the skirt portion and the outer surface of the capillary tube in the mounted position of the cap, each said closure cap further comprising a skirt compression member having a passage defined therein for receiving said cap when mounted on said capillary tube, the cross section of said passage being sized so as to compress said skirt portion radially inwardly into frictional contact with the outer peripheral surface of the capillary tube when said cap skirt portion is inserted into said passage, whereby said end wall may be maintained in sealing engagement with a respective open tube end.

6. The blood sampling set according to claim 5 wherein said skirt compression member is connected to said skirt portion by flexible connecting means, said passage and said skirt portion extending substantially coaxially on opposite sides of said cap end wall.

7. The blood sampling set according to claim 6 wherein said passage is defined by an annular bead or ridge formed on an inner annular surface of said compression member.

8. The blood sampling set according to claim 7 wherein said annular ridge or bead is made from an elastic material.

9. In a blood sampling set of the type having an open ended capillary tube and a pair of closure caps for anaerobicly sealing both tube ends, wherein the improvement comprises: the closure caps, each closure cap having an end wall with an inner surface providing a sealing means for effecting a sealing engagement with a respective open end of said capillary tube, an annular skirt portion extending axially from said inner surface of said cap end wall for frictional engagement with said capillary tube and at least one venting passage extending from the ambient atmosphere to said inner surface of said cap end wall for ensuring essentially complete expulsion of air entrapped between said respective end of said respective capillary tube and said closure cap when said closure cap is mounted on said respective end of said capillary tube.

10. A blood sampling set according to claim 9, wherein said sealing means comprises a tapered stopper member extending axially from said inner surface of the cap end wall, said stopper member being adapted to be sealingly received in said respective open tube end.

11. A blood sampling set according to claim 9 wherein the cross section of the inner surface of said annular skirt portion is non-circular at least adjacent to said cap end wall so as to define said venting passage between the inner surface of said skirt portion and the outer peripheral surface of said capillary tube once said cap is mounted thereon.

12. The blood sampling set according to claim 11 wherein said cross section of the inner surface of said skirt portion is polygonal.

13. The blood sampling set according to claim 9 wherein the inner surface of said skirt portion defines a blind hole having an open end with a cross sectional area exceeding the cross sectional area of said hole adjacent to the cap end wall so as to facilitate insertion of said respective open tube end.

14. The blood sampling set according to claim 11 wherein said non-circular cross section is shaped so as to define a number of venting passages in the range of 3–6.

15. The blood sampling set according to claim 9 wherein the cross section of the inner surface of said annular skirt portion is circular at least adjacent to said cap end wall, said inner surface being adapted to fit snugly around the outer peripheral surface of the capillary tube, said venting passage being formed within the annular skirt portion of said cap.

* * * * *